(12) United States Patent
Erwin

(10) Patent No.: US 11,097,027 B2
(45) Date of Patent: Aug. 24, 2021

(54) SYSTEM AND METHOD FOR HOLDING AND SANITIZING WRITING IMPLEMENTS

(71) Applicant: Maura Elizabeth Erwin, Pottstown, PA (US)

(72) Inventor: Maura Elizabeth Erwin, Pottstown, PA (US)

( * ) Notice: Subject to any disclaimer, the term of this patent is extended or adjusted under 35 U.S.C. 154(b) by 0 days.

(21) Appl. No.: 16/932,664

(22) Filed: Jul. 17, 2020

(65) Prior Publication Data

US 2020/0345877 A1    Nov. 5, 2020

Related U.S. Application Data

(63) Continuation of application No. 15/457,961, filed on Mar. 13, 2017, now abandoned.

(51) Int. Cl.
| | | |
|---|---|---|
| *A61L 2/18* | (2006.01) | |
| *B43M 99/00* | (2010.01) | |
| *B43K 23/00* | (2006.01) | |
| *B43K 23/04* | (2006.01) | |

(52) U.S. Cl.
CPC .............. *A61L 2/18* (2013.01); *B43K 23/002* (2013.01); *B43K 23/04* (2013.01); *B43M 99/006* (2013.01); *A61L 2202/15* (2013.01)

(58) Field of Classification Search
CPC ..... A61L 2/16; A61L 2/18; A61L 2/26; B43K 23/00; B43K 29/00
See application file for complete search history.

(56) References Cited

U.S. PATENT DOCUMENTS

| | | |
|---|---|---|
| 816,959 A | 4/1906 | Briganti |
| 5,683,655 A | 11/1997 | Carter |
| 5,882,667 A | 3/1999 | Jones |
| 6,039,928 A | 3/2000 | Roberts |
| 6,142,297 A | 11/2000 | Price |
| 6,270,275 B1 | 8/2001 | Martz |
| 8,058,629 B2 | 11/2011 | Long |
| 8,357,914 B1 | 1/2013 | Caldwell |
| 8,491,849 B2 * | 7/2013 | Hermiz ................. A61L 2/18 422/292 |
| 8,770,881 B2 | 7/2014 | Dam |
| 8,967,900 B2 | 3/2015 | Anderson et al. |
| 2010/0143494 A1 | 6/2010 | Scheuing |
| 2011/0030726 A1 | 2/2011 | Vaillancourt |
| 2013/0081660 A1 | 4/2013 | Roberts et al. |
| 2014/0245866 A1 | 9/2014 | Hadlock et al. |

* cited by examiner

*Primary Examiner* — Timothy C Cleveland
(74) *Attorney, Agent, or Firm* — LaMorte & Associates, P.C.

(57) ABSTRACT

A system and method for holding and sanitizing handheld implements. The system uses a container filled with a body of open cell foam. The body of the open cell foam has hollow shafts formed therein for holding the implements. The hollow shafts in the body of open cell foam are accessible through the open top of the container. A volume of a liquid disinfectant is poured into the container. The liquid disinfectant is at least partially absorbed by the body of open cell foam. This moistens the walls of the hollow shafts with disinfectant. As handheld implement is inserted into a hollow shaft, it is physically wiped and coated with the liquid disinfectant without being submerged in liquid disinfectant. When the implement is drawn out of the tubular shaft, it is clean, sanitized and ready to use without the need to dry.

11 Claims, 4 Drawing Sheets

SYSTEM AND METHOD FOR HOLDING AND SANITIZING WRITING IMPLEMENTS

RELATED APPLICATIONS

This application is a continuation of U.S. patent application Ser. No. 15/457,961, filed Mar. 13, 2017.

BACKGROUND OF THE INVENTION

1. Field of the Invention

In general, the present invention relates to systems and methods that are used to disinfect the exterior of writing implements, such as pens, pencils and markers. More particularly, the present invention relates to systems and method that expose the exterior of writing implements to chemical disinfectants.

2. Prior Art Description

Writing implements, such as pens, pencils and markers, are utilized by being held in a writer's hand. As a consequence, the writing implement is contaminated with all the bacteria, viruses and other microbials that are present on the user's hand. Furthermore, writing implements are often placed behind the ear, held in the mouth, thrown into storage draws, placed into pencil cups, and dropped on the floor. Each one of these environments contains numerous microbial contaminants that are transferred to the writing implement. Many writing implements contain numerous grooves, contours, seams, clips, and materials that can harbor microbial contamination after exposure.

In a clean environment, such as a doctor office or a research laboratory, a person may wash their hands and put on protective gloves to prevent cross contamination. However, as soon as that person reaches for a pen or pencil to write down a note, the gloved hands become contaminated. Accordingly, the use of writing implements can be a significant cause of cross contamination in an otherwise clean environment.

There are many systems for disinfecting handheld objects. For example, a barber will place combs and scissors in an alcohol solution, such as Barbacide® between customers. This sanitizes the combs and scissors and prevents microbial contamination and parasite contamination from customer to customer. However such disinfecting systems cannot be used to disinfect most writing implements. Most pens and markers contain a liquid ink that is in an alcohol solution. Once the pen or marker is user to write, the alcohol rapidly evaporates from the dispensed ink and the ink quickly dries to the touch. Since the ink is soluble in alcohol, it will be understood that if a pen or marker where to be placed in a cup of disinfectant that contains alcohol, the ink in the pen or marker would run, therein destroying the pen or marker. Furthermore, if submerged in any liquid disinfectant, pens and markers contain hollows in their structure that would fill with the liquid. Once removed from the liquid disinfectant, the liquid disinfectant in the various hollows would leak from the pen or marker and ruin the paper being written upon.

In the prior art, devices have been developed that attempt to disinfect writing implements without causing the ink to run. For example, in U.S. Pat. No. 8,357,914, to Caldwell, writing implements are disinfected by being exposed to ultraviolet light. The problem with such systems is that ultraviolet light sources produce a significant amount of heat. The light energy and the heat energy combine to heat the ink within a pen or marker. This can cause the ink to expand and leak out of the pen or marker. Furthermore, the heat and light energy tends to cause the alcohol carrier in the inks to prematurely evaporate. As such, a pen or marker can prematurely run dry. Lastly, ultraviolet light degrades plastic, especially foam plastic. Many pens have sections of foam plastic on there exterior for comfort. Exposure to ultraviolet light rapidly causes such surface to degrade and disintegrate, therein ruining the pen.

In U.S. Pat. No. 5,683,655 to Carter, a system is discloses where a writing implement is wiped against a material that is soaked with a disinfectant. The problem with such a system is that it is not passive. Rather, the system requires a user to manipulate the writing implement completely through a tube each time the writing implement is touched. This takes a considerable amount of effort and time. Consequently, in a real world application, the process would be often skipped. Furthermore, when passed through the tube of disinfectant, a pen or pencil may only spend a second or two in actual contact with the disinfecting surfaces. This is insufficient time to sanitize a pencil, pen or marker having many crevasses that harbor contamination. In addition, the system does nothing to keep the writing implement clean and sanitary when the writing implement is not in use and is rested upon a contaminated surface.

A need therefore exists for a system and method of sanitizing a writing implement and keeping the writing implement clean as it awaits use. A need also exists for a system and device for sanitizing a writing implement that completely sanitizes the writing implement in a passive manner without harming the writing implement. These needs are met by the present invention as described and claimed below.

SUMMARY OF THE INVENTION

The present invention is a system and method for holding and sanitizing writing implements while they await use. The system uses a container having a closed bottom and an open top. The container can be self-standing or a smaller version, such as a pocket protector. The container is filled with a body of open cell foam. The body of open cell foam has a plurality of hollow shafts formed therein for holding writing implements. The hollow shafts in the body of open cell foam are accessible through the open top of the container. To limit evaporation losses, the open top of the container is covered with a cap. Access holes are formed through the cap directly above the tubular shafts. In this manner writing implements can be inserted into the tubular shafts directly through the cap.

A volume of a liquid disinfectant is poured into the container. The liquid disinfectant is at least partially absorbed by the body of open cell foam. This moistens the walls of the hollow shafts with disinfectant. As a writing implement is inserted into a hollow shaft, it is physically wiped and coated with the liquid disinfectant without being submerged in liquid disinfectant. When the writing implement is drawn out of the tubular shaft, it is clean, sanitized and ready to use without the need to dry.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention disinfecting system and method can be embodied in many ways, only two exemplary embodiments are presented for discussion. The exemplary embodiments set forth two of the best modes contemplated for practicing the invention, However, the embodiments are merely exemplary and should not be considered a limitation when interpreting the scope of the appended claims.

Figure 1:
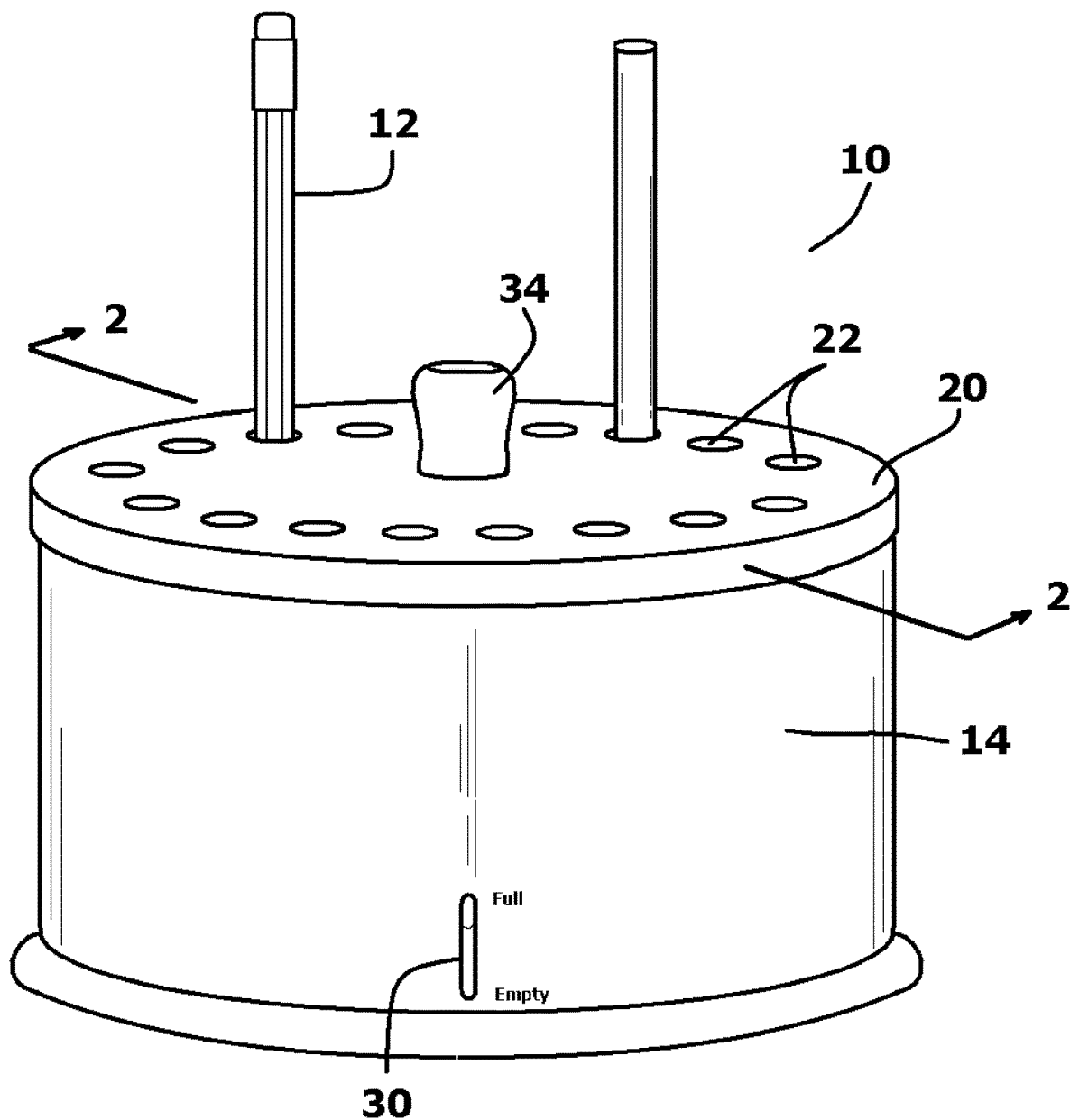
FIG. 1 is a perspective view o of an exemplary embodiment of a sanitizing station shown in conjunction with some writing implements.
Figure 2:
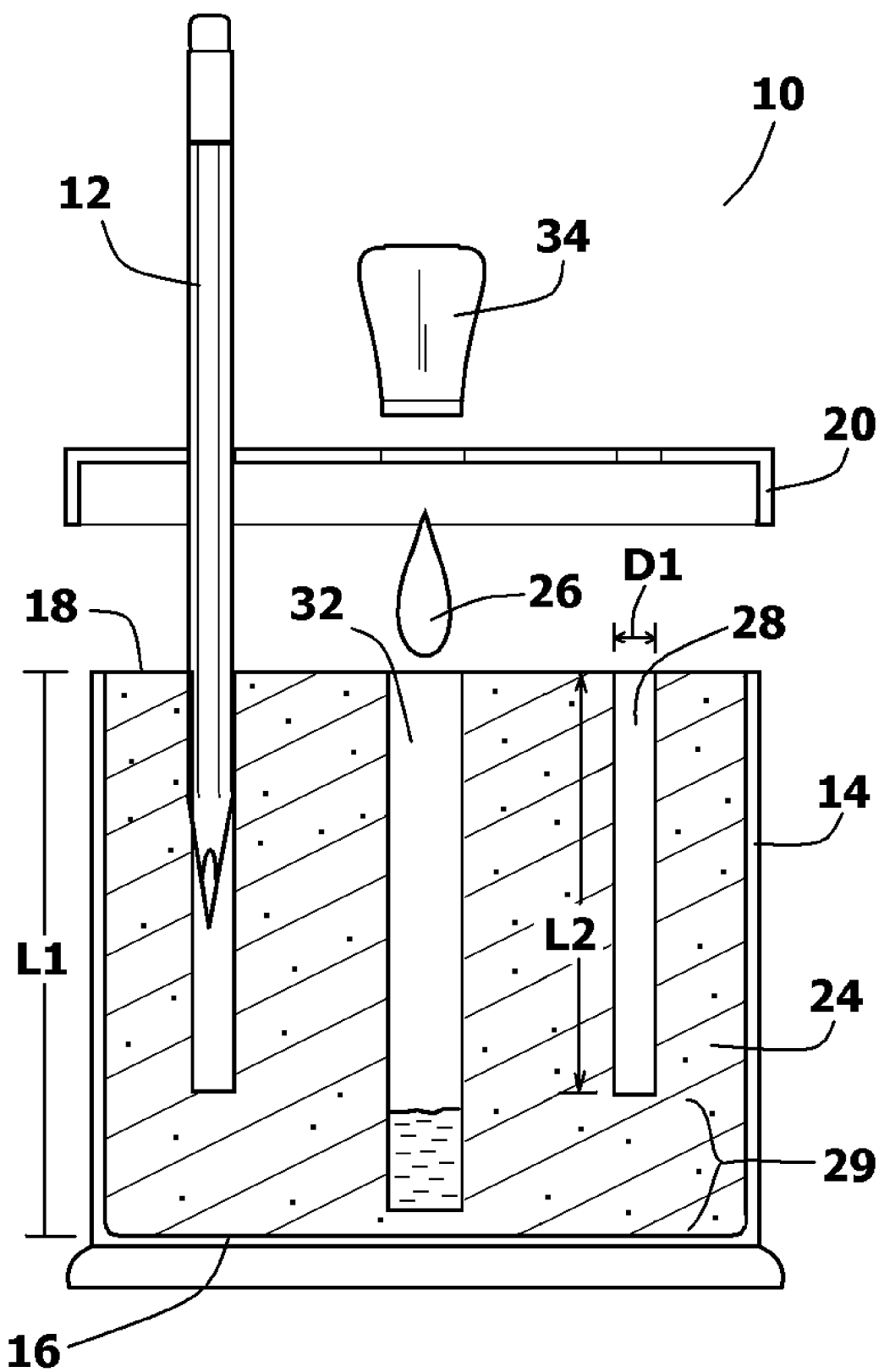
FIG. 2 is a cross-sectional view of the exemplary embodiment of FIG. 1.

Referring to FIG. 1 and FIG. 2, a sanitizing station 10 is shown that can be used to disinfect a variety of writing implements 12, such as pencils pens and markers. The sanitizing station 10 consists of a container 14. The container 14 has an overall length L1 between a closed bottom 16 and an open top 18. The open top 18 is partially covered by a cap 20. The cap 20 contains a plurality of access holes 22. The access holes 22 are sized so that writing implements 12 can pass trough the cap 20 and into the container 14 when not in use.

A body of open cell foam 24 is disposed within the container 14 under the cap 20. The body of open cell foam 24 is preferably a synthetic foam material, such as a polyurethane foam that is mixed with softening agents to remain pliable. The body of open cell foam 24 is exposed to a volume of liquid disinfectant 26 within the confines of the container 14. The liquid disinfectant 26 is insufficient to fully saturate the body of open cell foam 24. Rather, the liquid disinfectant 26 keeps the body of open cell foam 24 damp with the liquid disinfectant 26, using a wicking action, which is later explained.

The body of open cell foam 24 fills or mostly fills the container 14. Hollow shafts 28 are formed in the body of open cell foam 24 under the access holes 22 in the cap 20. The hollow shafts 28 are parallel. Each of the hollow shafts 28 has a length L2 which is shorter than the overall length L1 of the container 14. The result is a solid area 29 within the body of open cell foam 24 that exists below the hollow shafts 28 but above the closed bottom 16 of the container 14.

Each hollow shaft 28 has a preferred diameter D1 between 5 mm and 10 mm. As such, when a writing implement 12 is advanced into a hollow shaft 28 through an access hole 22 in the cap 20, the writing implement 12 will be contact the walls that define the hollow shaft 28 and will be moistened by the liquid disinfectant 26 carried by the body of open cell foam 24. By being in contact with the liquid disinfectant 26, the writing implement 12 is sterilized. The writing implement 12 is stored in the confines of the hollow shaft 28 when not in use. As such, the writing implement 12 will remain in contact with the body of open cell foam 24 and the liquid disinfectant 26 it carries for prolonged periods of time. Such exposure is sufficient to kill most all contamination present on the writing implement 12.

Many liquid disinfectants can be used. However, The choice of the liquid disinfectant 26 is very important to make the sanitizing station 10 a viable commercial product. The liquid disinfectant cannot be alcohol based or a petroleum by-product, such as a ketone. If it were, the disinfectant could dissolve the ink of the writing implement and/or the plastic used to fabricate the writing implement. Also, the disinfectant must be colorless so as not to stain the hand and/or paper to which a sanitized writing implement is applied. The disinfectant also cannot be unstable over short periods of time, such as is hydrogen peroxide. Otherwise, the disinfectant would loose its effectiveness over prolonged periods of use. It is also preferred that the disinfectant be odorless, non-toxic, and non-reactive to materials. For example, if the disinfectant were a dilution of chlorine, the disinfectant would have a strong smell, would be a danger to a user who touched his/her eyes, and could discolor writing material or died clothing that it inadvertently contacts.

Taking into account the needed properties of the disinfectant, the preferred liquid disinfectant 26 for use in the sanitizing station 10 is an aqueous solution of silver di-hydrogen citrate. An aqueous solution of silver di-hydrogen citrate containing between 50 ppm and 100 ppm silver ions, is colorless and mostly odorless. Any mild odor that may be present is that of citrus and is pleasant to most consumers. Silver di-hydrogen citrate provides a broad spectrum antimicrobial activity and is effective against bacteria, fungi and viruses including pathogenic microorganisms. The antimicrobial properties of silver are well known. In order for silver to be effective in killing microorganisms, it must be in an ionic form. Silver di-hydrogen citrate is a complex of one silver ion weakly bound to one citrate ion having the molecular complex $AgC_6H_7O_7$. Silver di-hydrogen citrate provides a stabilized form of silver ion in an organic acid (citric acid). The bioavailability of the ions allows for silver di-hydrogen citrate to be rapidly effective against a broad spectrum of bacteria, viruses and fungi. Silver di-hydrogen citrate utilizes a multiple prong attack against microorganisms. Silver di-hydrogen citrate targets an organism's cell membrane. Silver ions are highly attracted to sulfur-containing thiol groups found in metabolic and structural proteins bound to the membrane surface. Silver di-hydrogen citrate targets these critical proteins and destroys their structure. This disruption of the organisms' membrane function and integrity lyses the membrane and the organism dies. In addition to supporting the silver ion, citrate plays a key part in the effectiveness of silver di-hydrogen citrate. Bacteria are actually attracted to silver di-hydrogen citrate because they recognize citric acid as a food source. This allows silver di-hydrogen citrate to easily enter the microorganism through membrane transport proteins. Once inside the organism, silver di-hydrogen citrate binds to DNA and intracellular proteins causing irreversible damage to the DNA and protein structure. Metabolic and reproductive functions halt, and the organism dies. Viruses are much smaller than bacterial and fungal cells and do not have metabolic activity. Viruses present fewer targets sites on which a biocide can act. Silver targets the viral envelope or capsid and the viral nucleic acid. Silver not only destroys the viral envelope, preventing the virus from attaching to a host cell, it also destroys the infectious component of the virus, the nucleic acid.

The sanitizing station 10 is design not to soak the writing implements 12 in the liquid disinfectant 26. This is accomplished by controlling the volume of the liquid disinfectant 26 present in the container 14. The volume of the liquid disinfectant 26 present in the container 14 can be determined by a quick visual inspection. A narrow vertical window 30 is formed in the wall of the container 14 near its closed bottom 16. The window 30 is either transparent or translucent enough to visually determine the fluid level within the container 14. The top of the window 30 is a length L3 below the open top 18 of the container 14. The length L3 from the open top 18 to the window 30 is longer than the length L2 of the hollow shafts 28. The result is that the window 30 corresponds in position to the solid area 29 within the body of open cell foam 24.

When the liquid disinfectant 26 is added to the container 14, the liquid disinfectant 26 is absorbed by the body of open cell foam 24. Once the body of open cell 24 foam reaches its saturation point, the liquid disinfectant 26 will pool in the bottom of the container 14. The level of the pooled liquid disinfectant 26 is visible through the window 30 in the container 14. To prevent any part of a writing implement 12 from soaking in liquid disinfectant 26, the level of the pooled liquid disinfectant 26 is always kept below the top of the window 30. In this manner, the level of the pooled liquid disinfectant 26 will be below the bottom of the hollow shafts 28 that hold the writing implements 12. Likewise, by observing the pooled liquid disinfectant 26 in the vertical window 30, a person can determine when the liquid disinfectant 26 is running dry and can add more liquid disinfectant 26 as needed.

A central filler bore 32 is formed in the body of open cell foam 24. The central filler bore 32 is larger than the hollow shafts 28 and descends deeper into the body of open cell foam 25 than do the hollow shafts 28. The central filler bore 32 is used to introduce more of the liquid disinfectant 26 into the container 14. To add liquid disinfectant 26, a plug 34 on the cap 20 is removed to expose the central filler bore 32. The liquid disinfectant 26 is the pored into the central filler bore 32 until the level of the liquid disinfectant 26 viewed through the vertical window 30 is adequate. Once properly filled, the plug is replaced.

Writing implements 12 are set into the hollow shafts 28 through the access holes 22 in the cap 20. Once in a hollow shaft 28, the writing implements 12 can be left indefinitely. The writing implements 12 will not fill with the liquid disinfectant 26 because the writing implements 12 are held above the pooling level of the liquid disinfectant 26. The writing implements 12 are, however, dampened by the liquid disinfectant 26 due to the wicking action of the body of open cell foam 24. Due to the long durations of the writing implements 12 in the sanitizing station 10, which can be hours, days or weeks, the writing implements 12 are encased in a disinfecting environment that disinfects all surfaces in and around the writing implements 12. Furthermore, as writing implements 12 are placed into the hollow shafts 28 and pulled out of the hollow shafts 28, the exterior of the writing implements 12 are automatically subjected to a wiping action that wipes dirt and debris off of the writing implements 12. The result is a passive system that automatically cleans and sanitizes writing implements 12 just by placing the writing implements into the sanitizing station 10 when not in use.

Figure 3:
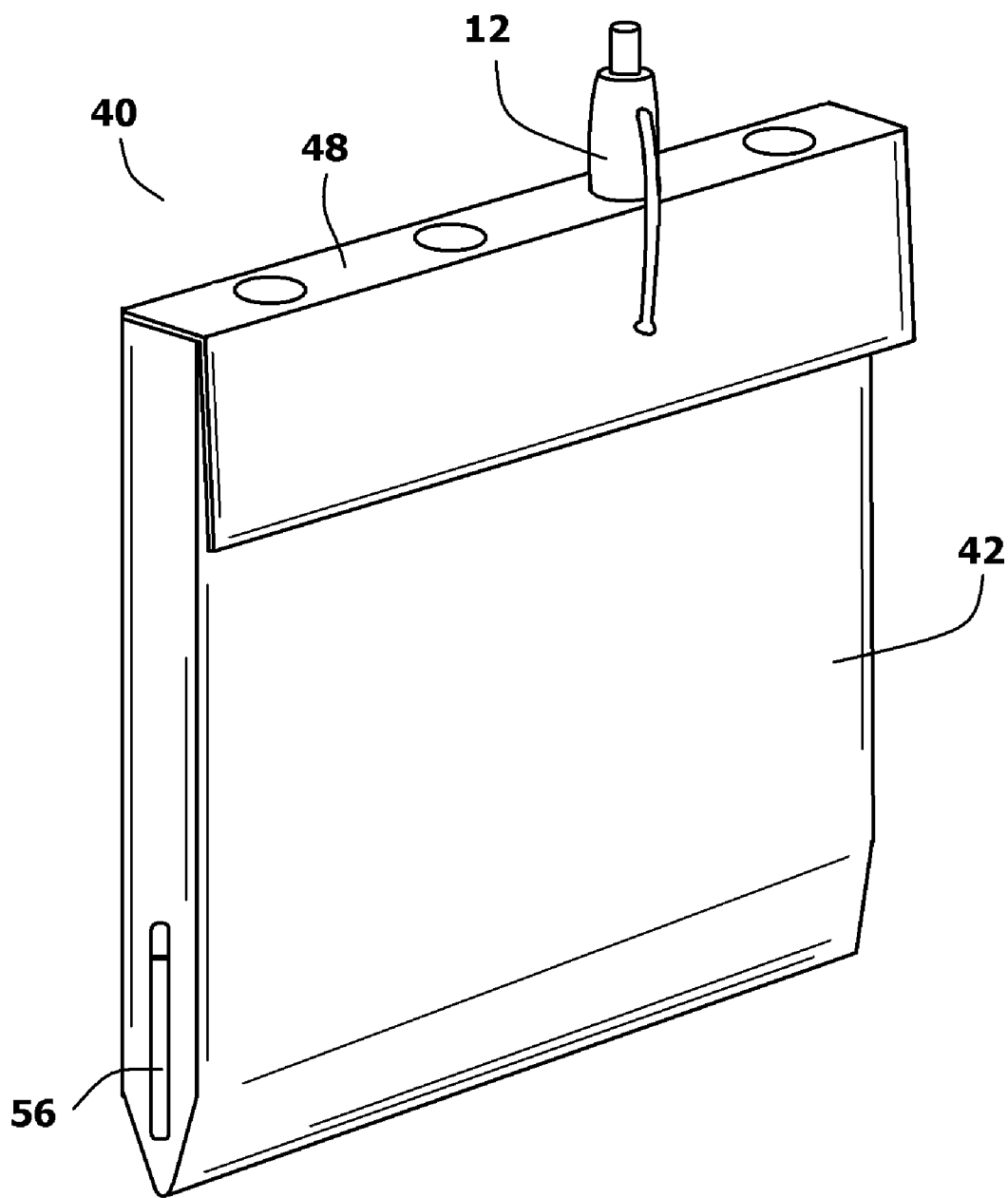
FIG. 3 shows the present invention configured as a pocket protector and shown in conjunction with some writing implements.
Figure 4:
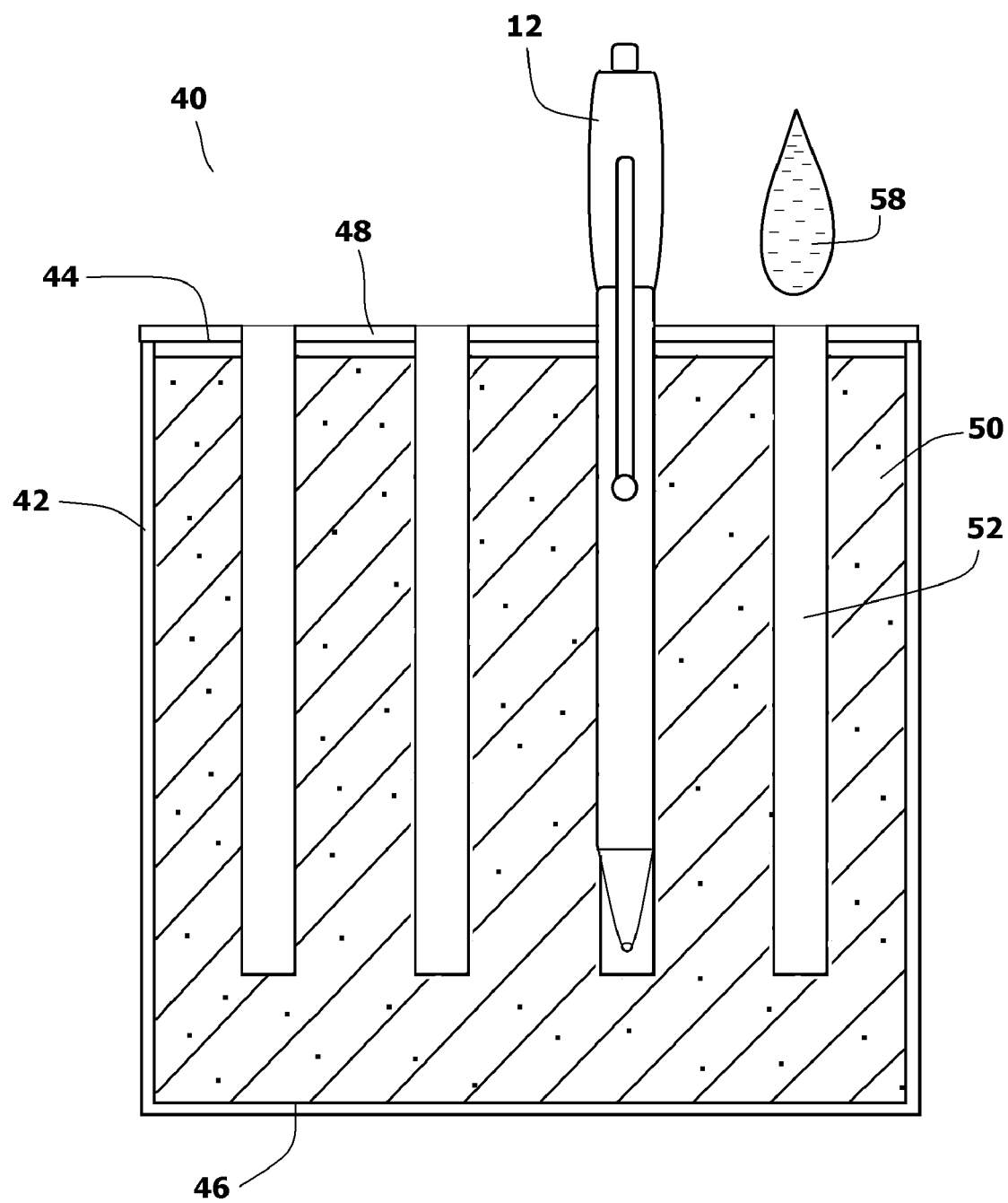
FIG. 4 is a cross-sectional view of the exemplary embodiment of FIG. 3.

Referring now to FIG. 3 and FIG. 4, an alternate embodiment of the present invention is shown. In this embodiment, the present invention is configured as a pocket protector 40. The pocket protector 40 is useful to doctors and other healthcare professionals that may travel from room to room in hospital or clinics and are concerned with cross contamination.

The pocket protector 40 has a liquid impervious case 42. The case 42 has an open top 44 and a closed bottom 46. The open top 44 of the case 42 is covered by a flap closure 48. Under the flap closure 48, the case 42 is filled with open cell foam material 50. Hollow shafts 52 are formed in the open cell foam material 50. The hollow shafts 52 are parallel. The hollow shafts 52 are accessible through access opening 54 in the flap closure 48.

A window 56 is formed in the case 42 near its closed bottom 46. The window 56 enables a person to visualize the level of any pooled liquid within the case.

The case 42 is partially filled with a liquid disinfectant 58. The volume of the liquid disinfectant 58 is controlled so that it does not pool to any level higher than the window 56. The liquid disinfectant 26 keeps the open cell foam material 50 damp through absorption and a wicking action from the pooled liquid disinfectant 58.

Writing implements 12 are set into the hollow shafts 52 through the access openings 54 in the flap closure 48. Once in a hollow shaft 52, the writing implements 12 can be left indefinitely. The writing implements 12 will not fill with the liquid disinfectant 58 because the writing implement is held above the pooling level of the liquid disinfectant 58. The writing implements 12 are, however, dampened by the liquid disinfectant 58 due to the wicking action of the open cell foam material 50. This sanitizes the writing implements 12. Furthermore, as a writing implement 12 is placed into a hollow shaft 52 and pulled out of a hollow shaft 52, the exterior of the writing implement 12 is automatically subjected to a wiping action that wipes dirt and debris off of the writing implement 12. The result is a passive system that automatically cleans and sanitizes writing implements 12 just by placing the writing implement into the pocket protector 40 when not in use.

It will be understood that the embodiments of the present invention that are illustrated and described are merely exemplary and that a person skilled in the art can make many variations to those embodiments. For instance, different disinfection solutions can be used. Likewise, different formulations of open cell foam can be used. The appearance of the container is understood to be a matter of design choice. All such embodiments are intended to be included within the scope of the present invention as defined by the claims.

What is claimed is:

1. A device for holding and sanitizing handheld implements, comprising:
    a container having a closed bottom and an open top, wherein a first length exists between said open top and said closed bottom;
    a body of open cell foam disposed in said container;
    a plurality of hollow shafts formed in said body of open cell foam are accessible through said open top of said container, and wherein each of said plurality of hollow shafts has a second length that is less than said first length, therein leaving an area uninterrupted by said plurality of hollow shafts within said body of open cell foam that is interposed between said plurality of hollow shafts and said closed bottom of said container; and
    a volume of a liquid disinfectant sufficient to partially fill said container to said area of said body of open cell foam between said plurality of hollow shafts and said closed bottom of said container, wherein said body of open cell foam wicks at least some of said volume of said liquid disinfectant around each of said plurality of hollow shafts.

2. The device according to claim 1, wherein said liquid disinfectant includes an aqueous solution of silver di-hydrogen citrate.

3. The device according to claim 1, wherein said container has a cover that covers said open top of said container, wherein said cover has access holes that align over said plurality of hollow shafts in said body of open cell foam.

4. The device according to claim 1, further including a fill bore formed in said body of open cell foam, wherein said fill bore extends into said area of said body of open cell foam between said plurality of hollow shafts and said closed bottom of said container.

5. The device according to claim 1, wherein said body of open cell foam fills said container.

6. The device according to claim 1, wherein said volume of liquid disinfectant fully saturates said area of said body of open cell foam between said hollow shafts and said closed bottom of said container.

7. The device according to claim 1, further including a window in said container that shows a level for said liquid disinfectant within said container.

8. A device for holding and sanitizing writing implements, comprising:
   a container having an open top and a closed bottom;
   open cell foam material filling said container, said open cell foam material having a plurality of hollow parallel shafts formed therein, wherein an area of said open foam material exists between said plurality of hollow parallel shafts and said closed bottom of said container that is uninterrupted by said plurality of hollow parallel shafts;
   a closure for covering said open top of said container, wherein said closure has access holes formed therethrough that provide direct access to said hollow parallel shafts in said open cell foam material; and
   a liquid disinfectant held within said container at a volume that partially saturates said area of said open foam material, wherein said open foam material wicks said liquid disinfectant around said plurality of hollow parallel shafts.

9. The device according to claim 8, wherein said liquid disinfectant includes an aqueous solution of silver di-hydrogen citrate.

10. The device according to claim 9, further including a fill bore formed in said open cell foam material, wherein said fill bore extends into said area of said open cell material between said plurality of hollow parallel shafts and said closed bottom of said container.

11. The device according to claim 8, further including a window in said container that shows a level for said liquid disinfectant within said container.

* * * * *